(12) United States Patent
Zamost

(10) Patent No.: US 6,750,045 B2
(45) Date of Patent: Jun. 15, 2004

(54) FERMENTATION MEDIUM AND METHOD

(75) Inventor: Bruce L. Zamost, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 10/201,168

(22) Filed: Jul. 23, 2002

(65) Prior Publication Data

US 2003/0059925 A1 Mar. 27, 2003

Related U.S. Application Data

(60) Provisional application No. 60/307,302, filed on Jul. 23, 2001.

(51) Int. Cl.[7] .................................................. C12P 21/02
(52) U.S. Cl. .............................. 435/69.6; 435/254.21; 435/255.2
(58) Field of Search ........................... 435/69.6, 254.21, 435/255.2

(56) References Cited

U.S. PATENT DOCUMENTS

| 5,612,456 A | | 3/1997 | Bishop et al. ............... 530/381 |
| 5,849,559 A | * | 12/1998 | Van Der Wouw et al. .. 435/209 |
| 6,306,635 B1 | * | 10/2001 | Van Den Broeck et al. 435/209 |

OTHER PUBLICATIONS

Bishop, P.D. et al., *Biochem* 29(7):1861–1869, 1990.

* cited by examiner

*Primary Examiner*—James Ketter
(74) *Attorney, Agent, or Firm*—James M. Bogden; Paul G. Lunn

(57) ABSTRACT

A yeast fermentation medium that does not contain yeast cell extract but is comprised of a mixture of oleic acid, lactic acid and palmitic acid. Using this fermentation medium yields of factor XIII were increased 250%.

9 Claims, 1 Drawing Sheet

FERMENTATION MEDIUM AND METHOD

This claims priority under 35 U.S.C. §119 (e) of U.S. provisional application No. 60/307,302 filed Jul. 23, 2001.

BACKGROUND OF THE INVENTION

The teachings of all of the references cited herein are incorporated in their entirety herein by reference.

A number of fermentation methods have been developed to produce recombinant polypeptides such as recombinant (r) (h) factor XIII in yeast. [See Bishop et al. *Biochem.* 29:1861 (1990).] While yeast tends to be a good host cell to produce many recombinant proteins, to obtain high yields of the polypeptide, it has been necessary to add yeast cell extract to the fermentation medium. However, yeast extract is expensive. Prior art efforts to produce a fermentation medium that does not contain yeast cell extract have been disappointing because the resultant yields of the recombinant protein are drastically reduced. Thus, there is a need to produce a yeast cell culture medium that does not contain yeast cell extract, but that can nonetheless be used to produce recombinant proteins in yeast resulting in high yields of the recombinant protein.

DESCRIPTION OF THE INVENTION

Figure 1:
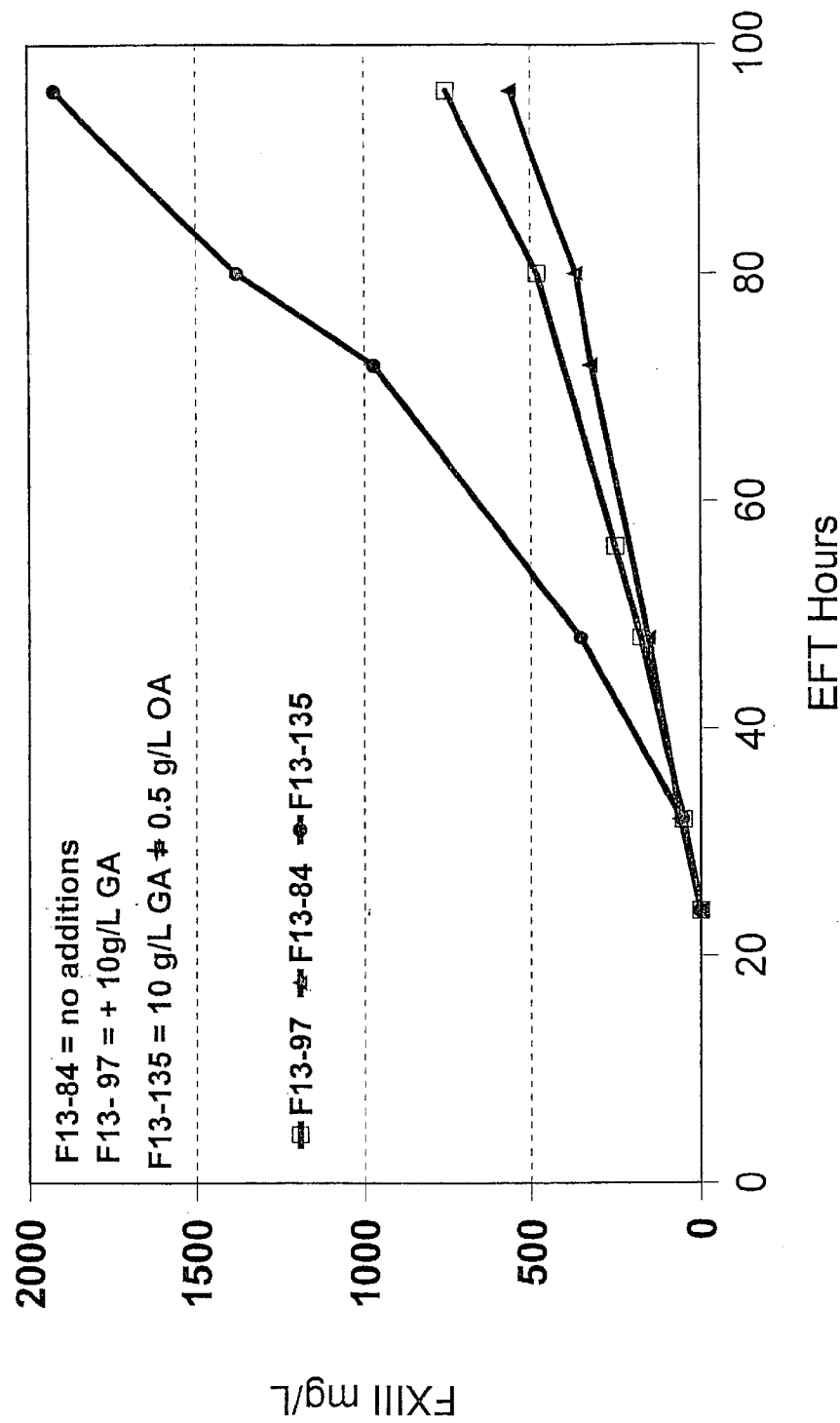
FIG. 1 graphically shows a comparison of the yields of rh factor XIII expressed in *S. cerevisiae* using various fermentation media.

The present invention fills this need by providing for a defined yeast fermentation medium recipe that does not contain yeast cell extract and is comprised of organic acids, preferably oleic acid, lactic acid and palmitic acid. The yields of recombinant (r) human (h) factor XIII obtained using *S. cerevisiae* grown in rich medium containing 3% yeast extract range were 1750 mg/L with a dry cell weight of 72.5 g/L. The yields of factor XIII in the same recipe minus the yeast extract were 546 mg/L with a dry cell weight of 62.5 g/L. The addition of 10 g/L glutamic acid improved the factor XIII yields to 754 mg/L and the dry cell weight (DCW) to 73.4 g/L.

While the growth yields obtained with the defined recipe plus glutamic acid were the same as obtained in the 3% yeast extract containing recipe, the factor XIII yields were less than 50%. A number of additives such as additional amino acids were tried, but the yields were not improved. During anaerobic fermentation of *S. cerevisiae*, compounds such as Tween 80 (poly sorbate mono oleate) and ergosterol are added to improve growth. A mixture of organic acids comprised of oleic acid, lactic acid and palmitic acid was added to the minimal medium (#7 of table 1) along with 10 g/L glutamic acid to improve rh factor XIII yields. The yield of factor XIII improved 250% by the addition of the organic acid mix comprised of oleic acid, lactic acid and palmitic acid.

The present invention also encompasses a method for producing a heterologous protein from yeast comprising growing a yeast containing DNA that expresses a heterologous protein in the fermentation medium of the present invention.

The recipes and feeding schemes are described below.

Example 1

Fermentation Methods Using Defined Medium for rhFactor XIII Production by *Saccharomyces cerevisiae*

Scope of Method

This method outlines a new fermentation processes for the production of factor XIII by *Saccharomyces cerevisiae* transfected with a vector encoding rh factor XIII. The process is a glucose fed batch fermentation utilizing a completely defined fermentation medium. The medium is supplemented with glutamic acid to increase growth over the basic defined recipe. It was found that the addition of 0.5 g/L of an organic acid mix containing oleic acid, lactic acid and palmitic acid at a ration of 6:3:1 in 100% EtOH, increased factor XIII yields by 250%. The yields in the defined medium are higher than obtained with the same basic recipe containing 30 g/L yeast extract.

Inoculum Development

A two-stage seeding procedure was used. Both stages were run in shake flask culture.

1. 500 ml baffled shake flasks were prepared with 100 ml of seed medium #9 (see table 1). Autoclave flasks, and after cooling aseptically add the glucose and vitamin solutions. To each flask 0.4 ml of seed medium contain *S. cerevisiae* transfected with a vector contain a polynucleotide encoding rh factor XIII were added. The flasks were incubated with shaking at 30° C., 250 rpm.
2. After 64 hours growth, 12.5 mls of cell culture were transferred to a 2.0 L baffled shake flask containing 250 ml of seed medium #9. The OD (optical density) 600 nm should be between 7 to 10 OD units. The flasks were incubated with shaking at 30° C., 250 rpm. Alternatively, inoculate a seed fermentor prepared with seed medium #9 with a 5% v/v inoculum.

Production Fermentors

The fermentation methods were developed using New Brunswick Scientific's BioFlo 3000 fermentation systems. The BioFlo 3000 fermentors have the usual temperature and pH control as well as DO (dissolved oxygen) control. The DO control cascade utilizes an initial increase in agitation speed (350–950 rpm), followed by an increase in aeration (aeration left constant at 1 vvm/starting volume), and followed by oxygen sparging (not normally required). The vessels have a 6.6 L maximum capacity, but the fermentations usually only reach the 5.0 liter level. The vessels are initially prepared with 3.0 liters of media. This has required the upper impeller to be lowered just below the 3.0 liter level. While this may have some negative effects on oxygen transfer, unwanted foaming is eliminated.

1. Fermentation vessels were prepared with 3.0 liters of recipe #7 or #8 (see table 1). The vessels were sterilized for 45 minutes at 121° C. in an autoclave. The vessels were allowed to cool and equilibrate overnight at 30° C.
2. After equilibration, the glucose and vitamin stocks were added to the vessel. The organic acid mixture was added at this time also. A sample was taken and the pH checked off line. Online fermentation pH values were then calibrated. The pH controller was set to pH 5.0. Only $NH_4OH$ [5 N] is used. No acid is required.
3. Agitation is set to 350 rpm and aeration to 1 vvm. The % DO saturation is calibrated to 100%. The DO controller cascade is activated to maintain DO above 30% saturation.
4. The fermenter was inoculated with 250 ml of a 24 hour shake flask culture. The OD 600 should be between 6 to 8 OD units.
5. At 10 hours elapsed fermentation time (EFT), a glucose feed was initiated. The initial feed rate was 1.15 g glucose/L/Hr (6.4 g of 60% glucose/vessel/hour) and was ramped to a maximum rate of 9.2 g glucose/L/Hr at 72 hours. The maximum feed rate was then maintained until the end of the run (96 hours). Calculations on glucose feed rates were based on the initial starting volume of 3. 25 liters.

6. A 2.0 liter bottle with 1900 ml of 60% glucose (2100 g) and 300 ml of 5 N $NH_4OH$ were used per run.
7. At the end of the run the temperature was set to 18° C. and the yeast harvested without pH adjustment.

TABLE 1

Fermentation recipes for shake flasks, seed tank, and main tank

| Material | Seed Medium #9 Amount (g/L) | Fermentation Recipe #8 Amount (g/L) F13-120 | Fermentation Recipe #7 Amount (g/L) F13-135 |
|---|---|---|---|
| Yeast extract | | 30.0 | |
| Red Star 900 AG | | | |
| glutamic acid | 3.00 | | 10.0 |
| $[NH_4]2SO_4$ | 5.00 | 11.5 | 11.5 |
| $NH_4H2PO_4$ | | | |
| $K_2HPO_4$ | 8.70 | | |
| $KH_2PO_4$ | | 11.5 | 11.5 |
| $MgSO_4$—7H2O | 2.50 | 2.5 | 2.5 |
| KCl | | | |
| NaCl | 0.50 | | |
| $CaCl_2$—$2H_2O$ | 0.25 | 0.5 | 0.5 |
| Citric Acid | 4.20 | | 1.0 |
| T.M. (Table 2) | 5 mL | 10.0 | 20 |
| Antifoam KFO 880 | 0.1 mL | 0.1 ml | 0.1 ml |
| $diH_2O$ | 950 mL | 950 ml | 1.0 L |
| pH with NaOH to | 5.75 | 5.0 | 5.0 |
| 60% Glucose | 50.0 mL | 50.0 ml | 50.0 |
| Vitamins (Table 3) | 5.0 mL | 10.0 | 10.0 |

TABLE 2

FXIII trace metals (T.M.) recipe

| Material | Amount Needed |
|---|---|
| zinc chloride | 4.52 g |
| ferric chloride | 35.91 g |
| manganese chloride | 12.70 g |
| copper sulfate-$5H_2O$ | 1.46 g |
| cobalt chloride | 1.72 g |
| boric acid | 0.41 g |
| ammonium molybdate | 0.014 g |
| potassium iodide | 0.014 g |
| hydrochloric acid 37% | 67 ml |

Dissolve completely all medium components in 5.0 liters distilled $H_2O$.
Bring the final volume to 6.65 liters with distilled $H_2O$ or WFI (water for injection).
Store at 3–8° C.

TABLE 3

Vitamin solution (inoculum, seed, and main fermentor)

| Material | Amount Needed-Grams |
|---|---|
| biotin | 0.160 g |
| thiamine hydrochloride | 2.56 g |
| pyroxidine HCl | 2.56 g |
| inositol | 48.0 g |
| calcium pantothenate | 48.0 g |
| niacinamide | 1.92 g |
| folic acid | 0.32 g |

TABLE 3-continued

Vitamin solution (inoculum, seed, and main fermentor)

| Material | Amount Needed-Grams |
|---|---|
| riboflavin | 0.64 g |
| choline chloride | 3.20 g |

Dissolve completely in 2.5 liters of distilled $H_2O$ or WFI. Bring final volume to 3.20 with WFI and mix. Store at 3–8° C.

In an alternative formulation the only vitamins used were inositol, biotin, pantothenic acid and pyroxidine.

DISCUSSION

Production of factor XIII by *S. cerevisiae* in defined medium#7, with glutamic acid or glutamic acid plus 0.5 g/L OA is shown in FIG. 1. The production of rh factor XIII increased 250% with the addition of the organic acids. The growth rates of the two fermentations were similar and approx. 20% higher than obtained in fermentations without the glutamic acid.

Two similar processes for FXIII production are described. Fermentation F13-120 was grown in a defined medium plus 3% yeast extract. F13-135 was grown in a completely defined medium containing 10 g/L glutamic acid and 0.5 g/L organic acid mix. Both were supplied glucose at the same feed rate. While the fermentation in complex medium obtained 1700 mg/L, the fermentation on defined medium reached 1925 mg/L. This is an improvement without the need for yeast extract.

What is claimed is:

1. A yeast fermentation medium comprised of oleic acid, lactic acid and palmitic acid, wherein the fermentation medium does not contain yeast cell extract.

2. The yeast fermentation medium of claim 1 wherein the oleic acid, lactic acid and palmitic acid are present in the medium at a ratio of 6:3:1 respectively.

3. The yeast fermentation medium of claim 2 further comprised of at least one of the substances selected from the group consisting of glutamic acid, citric acid, $KH_2PO_4$, $CaCl_2$, glucose, $[NH_4]_2SO_4$, zinc chloride, ferric chloride, manganese, copper sulfate, cobalt chloride, boric acid, ammonium molybdate, potassium iodide, biotin, thiamine hydrochloride, pyroxidine HCl, inositol, calcium pantothenate, niacinamide, folic acid, riboflavin, choline chloride.

4. A yeast fermentation medium in solution comprised of oleic acid, lactic acid, palmitic acid, glutamic acid citric acid, potassium ions, calcium ions, zinc ions, ferric ions, manganese ions, biotin, thiamine, pyroxidine, inositol, niacinamide, folic acid, riboflavin and choline ions, and wherein the yeast fermentation medium does not contain yeast cell extract.

5. A method for growing yeast comprising inoculating the yeast in a yeast fermentation medium comprised of oleic acid, lactic acid, palmitic acid, glutamic acid, citric acid, potassium ions, calcium ions, zinc ions, ferric ions, manganese ions, biotin, pyroxidine, inositol, pantothenic acid and choline ions, and wherein the yeast fermentation medium does not contain yeast cell extract.

6. The method of claim 5 wherein the yeast is *Saccharomyces cerevisiae*.

7. A method for expressing a heterologous protein in yeast comprising inoculating yeast which have been transformed with DNA encoding the heterologous protein into a fermentation medium, said fermentation medium being comprised of oleic acid, lactic acid and palmitic acid and wherein the fermentation medium does not contain yeast cell extract.

8. The method of claim 7 wherein the heterologous protein is human factor XIII.

9. The method of claim 8 wherein the yeast is *Saccharomyces cerevisiae*.

* * * * *